(12) United States Patent
Korenko et al.

(10) Patent No.: US 12,171,844 B2
(45) Date of Patent: *Dec. 24, 2024

(54) METHOD OF PREPARING A RADIOACTIVE YTTRIUM PHOSPHATE PARTICLE SUSPENSION

(71) Applicant: Vivos, Inc., Richland, WA (US)

(72) Inventors: Michael Korenko, Pasco, WA (US); David Swanberg, Kennewick, WA (US)

(73) Assignee: Vivos, Inc., Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/638,559

(22) PCT Filed: Jun. 2, 2020

(86) PCT No.: PCT/US2020/035733
§ 371 (c)(1),
(2) Date: Feb. 25, 2022

(87) PCT Pub. No.: WO2021/002994
PCT Pub. Date: Jan. 7, 2021

(65) Prior Publication Data
US 2022/0288242 A1   Sep. 15, 2022

Related U.S. Application Data

(63) Continuation of application No. 16/459,466, filed on Jul. 1, 2019, now Pat. No. 11,478,557.

(51) Int. Cl.
*A61K 51/02*  (2006.01)
*A61K 51/12*  (2006.01)

(52) U.S. Cl.
CPC .......... *A61K 51/02* (2013.01); *A61K 51/1217* (2013.01)

(58) Field of Classification Search
CPC .......................... A61K 51/02; A61K 51/1217
See application file for complete search history.

(56) References Cited

U.S. PATENT DOCUMENTS

| | | |
|---|---|---|
| 6,296,831 B1 | 10/2001 | Weller et al. |
| 6,841,617 B2 | 1/2005 | Jeong et al. |
| 7,087,244 B2 | 8/2006 | Jeong et al. |
| 2001/0024636 A1 | 9/2001 | Weller et al. |
| 2002/0039552 A1 | 4/2002 | Sapiezko et al. |
| 2003/0144570 A1 | 7/2003 | Hunter |
| 2004/0228794 A1 | 11/2004 | Weller et al. |
| 2008/0214414 A1 | 9/2008 | Carroll et al. |
| 2014/0221198 A1 | 8/2014 | Nagao et al. |
| 2018/0280942 A1 | 10/2018 | Chen et al. |

FOREIGN PATENT DOCUMENTS

| | | |
|---|---|---|
| CN | 102 530 904 A | 7/2012 |
| CN | 104 692 350 A | 6/2015 |
| WO | 2010028048 | 3/2010 |

OTHER PUBLICATIONS

Liang, RC., Li, X., Shi, Y., Want, A., Sun, L., Li, WH., Li, YX., Effect of Water on Exenatide Acylation in Poly (lactide-co-glycolide) Microspheres, International Journal of Pharmaceutics, vol. 454, 344-353, 2013.
Agrawal, CM, Athanasiou, KA; Technique to Control pH in Vicinity of Biodegrading PLA-PGA Implants, J. Biomed. Mater. Res., vol. 38(2), 104-114, 1997.
Baumann, A., Piel, I., Hucke, F., Sandmann, S., Hetzel, T., Schwartz, T., Pharmacokinetics, excretion, distribution and metabolism of 60-kDa polyethylene glycol used in BAY 94-9027 in rats and its value for human prediction, Europ. J. of Pharm. Sci., vol. 130, 11-20, 2019.
Erbetta, CDC, Alves, RJ., Resende, JM., Freitas RFS., Sousa, RG., Synthesis and Characterization of Poly (D,L-lactide-co-glycolide) Copolymer. Journal of Biomaterials and Nanobiotechnology, vol. 3, 208-225, 2012.
Gervais, KJ., Evaluation of a biodegradable thermogel polymer for intraocular delivery of cyclosporine A to prevent posterior capsule opacification, PhD Thesis, The Ohio State University, 2017.
Ivens, IA., Achanzar, W., Baumann, A., Brandli-Baiocco, A., Cavagnaro, J., Dempster, M., Depelchin, BO., Rovira. AR., Dill-Morton, OL., Lane, JH., Reipert BM., Salcedo, T., Schweighardt, B., Tsuruda, LS., Turecek, PL, Sims, J., PEGylated bio-pharmaceuticals: current experience and considerations for nonclinical development. Toxicol. Pathol. vol. 43, 959-983, 2015.
Jain, RA., The Manufacturing Techniques of Various Drug Loaded Biodegradable Poly(lactideo-co-glicolideo)(PLGA) Devices, Biomaterials, vol. 21, 2475-2490, 2000.
Liang, RC., Li, X., Shi, Y., Want, A., Sun, L., Li, WH., Li, YS., Effect of Water on Exenatide Acylation in Poly (lactide-co-glycolide) Microspheres, International Journal of Pharmaceutics, vol. 454, 344-353, 2013.
Laycock, B., Nikolic, M., Colwell, JM., Gauthier, E., Halley, P., Bottle, S., George G., Lifetime Prediction of Biodegradable Polymers, Prog. Polym. Sci, vol. 71, 144-189, 2017.
Lee, SS., Hughes, P., Ross, AD., Robinson, MR., Biodegradable implants for sustained drug release in the eye. Pharm. Res., vol. 27, 2043-2053, 2010.
Ma, H., Chaoliang, H., Cheng, Y., Li, D., Gong, Y., Keu, J., Tian, H., Chen, X., PLK1shRNA and doxorubicin co-loaded thermosensitive PLGA-PEG-PLGA hydrogels for osteosarcoma treatment, Biomaterials, vol. 35, 8723-8734, 2014.
Manickavasagam; E., Oyewumi, MO., Critical assessment of implantable drug delivery devices in glaucoma management. J. Drug Deliv., vol. 2013, 1-12, 2013.
Metha, S., Shastri, V., Muthurajan, H., Recent Advancement in PLGA Nano Polymer Synthesis and its Applications, J of Nanomedicine Research, vol. 4, Issue 1, Jul. 2016.

(Continued)

*Primary Examiner* — Robert S Cabral
(74) *Attorney, Agent, or Firm* — Indiano Law Group LLC; E. Victor Indiano

(57) ABSTRACT

A method of preparing a radioactive yttrium salt particle suspension comprising multiple steps comprising: using a hydrothermal process wherein a solution of soluble yttrium salt, from the group of yttrium chloride, yttrium nitrate, yttrium sulfate, and yttrium bromide is combined with a solution of sodium phosphate having a stoichiometric excess of phosphate and a preferred pH when combined.

9 Claims, 1 Drawing Sheet

(56) References Cited

OTHER PUBLICATIONS

Peng, Y., Ang., M., Foo, S., Lee, WS., Ma, Z., Venkatraman, SS., Wong, TT., Biocompatibility and biodegradation studies of subconjunctival implants in rabbit eyes. PLoS ONE, vol. 6, e22057, 2011.

Shellekens, H., Hennink, WE., Brinks, V., The immunogenicity of polyethylene glyol: facts and fiction, Pharm. Res., vol. 30, 1729-1734, 2013.

Souza, MCM., Fialho, SL., Souza, PAF, Fulgencio, GO, Da Silve, GR, Silva-Cunha, A., Tacrolimus-loaded PLGA implants: In vivo release and ocular toxicity. Curr. Eye Res. vol. 39, 99-102, 2014.

Stevanovic, M., Maksin, T., Petkovic, J., Filipic, M., Uskokovic, D., An Innovative, Quick and Convenient Labeling Method for the Investigation of Pharmacological Behavior and the Metabolism of Poly(DL-lactide-coglycolide) Nanospheres, Nanotechnology, vol. 20, 1-12, 2009a.

Stevanovic, M., Uskokovic, D., Poly(lactide-co-glycolide)-Based micro and Nanoparticles for the Controlled Drug Delivery of Vitamins. Current Nanoscience, vol. 5, 1-14. 2009b.

Tarasevich, B, Gutowska, A., Li, XS, Jeong, B-M, The effect of polymer composition on the gelation behavior of PLGA-g-PEG biodegradable thermoreversible gels, J of Biomedical Materials Research Part A, 89(1):248-54, 2009.

Wang, P., Chu, W., Zhuo, X., Zhang, Y., Gou, J., Ren, T., He, H., Yin, T., Tang, X., Modified PLGA-PEG-PLGA thermosensitive hydrogels with suitable thermosensitivity and properties for use in a drug deliver system, J. Materials Chemistry B, Issue 8, 2017.

Webster, R., Didier, E., Harris, P., Siegel, N., Stadler, J., Tilbury, L., Smith, D., PEGylated proteins: evaluation of their safety in the absence of definitive metabolism studies. Drug Metab. Dispos. vol. 35, 9-16. 2007.

ISA/US Commissioner for Patents; International Search Report for PCT Patent Application No. PCT/US2020/35733 issued Sep. 8, 2020.

Hiroaki, Onada and Funamoto, Takehiro; Hydrothermal treatment for preparation of europium-lanthanum phosphates and exploration of their fluorescence properties; Journal of Materials Research and Technology; 2014:3 (2), pp. 122-128; http://dz.doi.org/10.1016/j.jmrt.2014 02.002.

First Official Action and search strategy of sister US ase U.S. Appl. No. 16/459,466 dated Oct. 1, 2020.

Final Official Action and search strategy of sister US ase U.S. Appl. No. 16/459,466 dated Apr. 13, 2021.

International Search report and Written Opinion of the International Search Authority PCT/US2020/035733.

Majeed Shafquat et al: "Dispersible crystalline nanobundles of YPO4 and Ln (Eu, Tb)-doped YPO4 : rapid synthesis, optical properties and bio-probe applications", Journal of Nanoparticle Research, vol. 17, No. 7, Jul. 16, 2015 (Jul. 16, 2015), pp. 1-15, XP035526460, ISSN: 1388-0764, DOI: 10.1007/S11051-015-3113-3.

Vanetsev AS et al: "Phase composition and morphology of nanoparticles of yttrium orthophosphates synthesized by microwave-hydrothermal treatment: The influence of synthetic conditions", Journal of Alloys and Compounds, vol. 639, Mar. 20, 2015 (Mar. 20, 2015), pp. 415-421, XP029156848, ISSN: 0925-8388, DOI: 10.1016/J.JALLCOM.2015.03.125.

CN 104 692 350 A (Inst Geochemistry Cas) Jun. 10, 2015 (Jun. 10, 2015), Machine Translation into English Language.

CN 102 530 904 A (Ganzhou Qian Dong Rare Earth Group COL TD) Jul. 4, 2012 (Jul. 4, 2012) Machine Translation into English Language.

European Patent Office, Sep. 29, 2023 Supplementary European Search Report for European Patent Application for Korenko et al EP 20 83 4229.

Baumann, A., Tureck, E., Prabhu, S., Dickmann, L., Sims, J., Pharmacokinetics, metabolism and distribution of PEGs and PEGylated proteins: quo vadis?, Drug Discov. Today, vol. 19, 1623-1631, 2014.

Jeffrey L. Schaal et al.; Injectable Polypeptide Micelles that form Radiation Crosslinked Hydrogels in Situ for Intratumoral Radiotherapy; J. Control Release Apr. 28, 2016; 58-66; Durham NC.

Pappalardo, DT., Mathisen, T., Finne-Wistrand, A., Biocompatibility of Resorbable Polymers: A Historical Perspective and Framework for the Future, Biomacromolecules, vol. 20, 1465-1477, 2019.

METHOD OF PREPARING A RADIOACTIVE YTTRIUM PHOSPHATE PARTICLE SUSPENSION

This application is a Section 371 Nationalization of Korenko et al PCT application no. PCT/US2020/035733, filed 2 Jun. 2020; and is a continuation of Korenko et al U.S. patent application Ser. No. 16/459,466 filed 1 Jul. 2019, both of which are hereby incorporated into this application by reference

FIELD AND BACKGROUND OF THE INVENTION

A method of preparing a radioactive yttrium phosphate particle suspension for the treatment of tumors including solid tumors.

Any patents and publications referred to herein are incorporated herein by reference

SUMMARY OF THE INVENTION

The method claimed is the preparation of radioactive yttrium phosphate particles of a size preferred for interstitial application in solid tumors.

BRIEF DESCRIPTION OF THE FIGURES

The foregoing and other features and advantages of the present invention will become more readily appreciated as the same become better understood by reference to the following detailed description of the preferred embodiment of the invention when taken in conjunction with the accompanying drawings, wherein.

Figure 1:
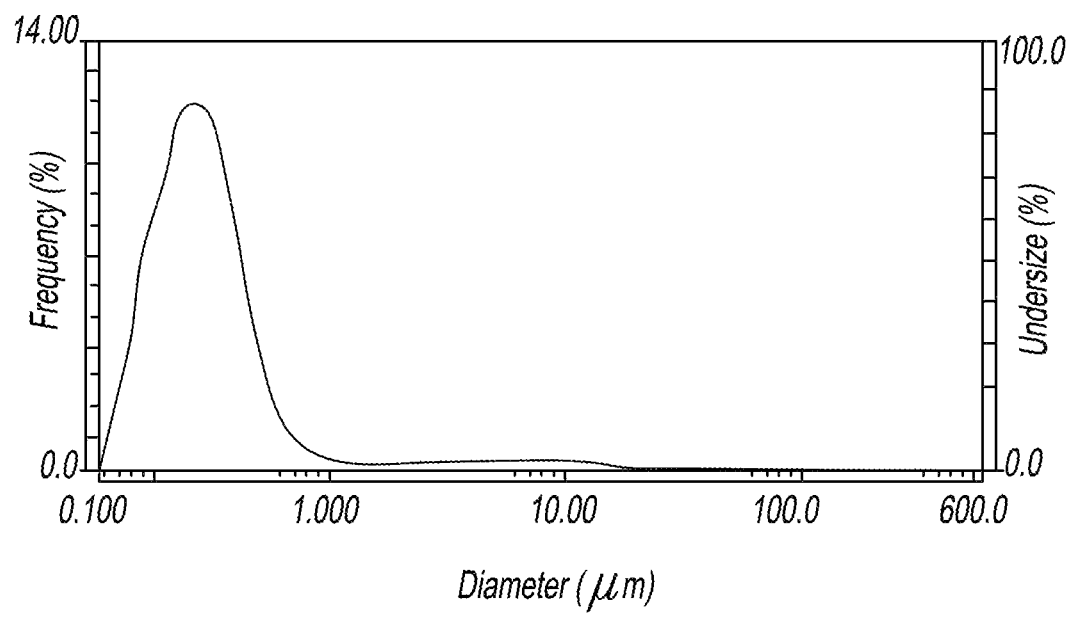
FIG. 1 illustrates particle size determined through the claimed process with pH of 7.35 yielding particle median size of 0.2450 μm.
Figure 2:
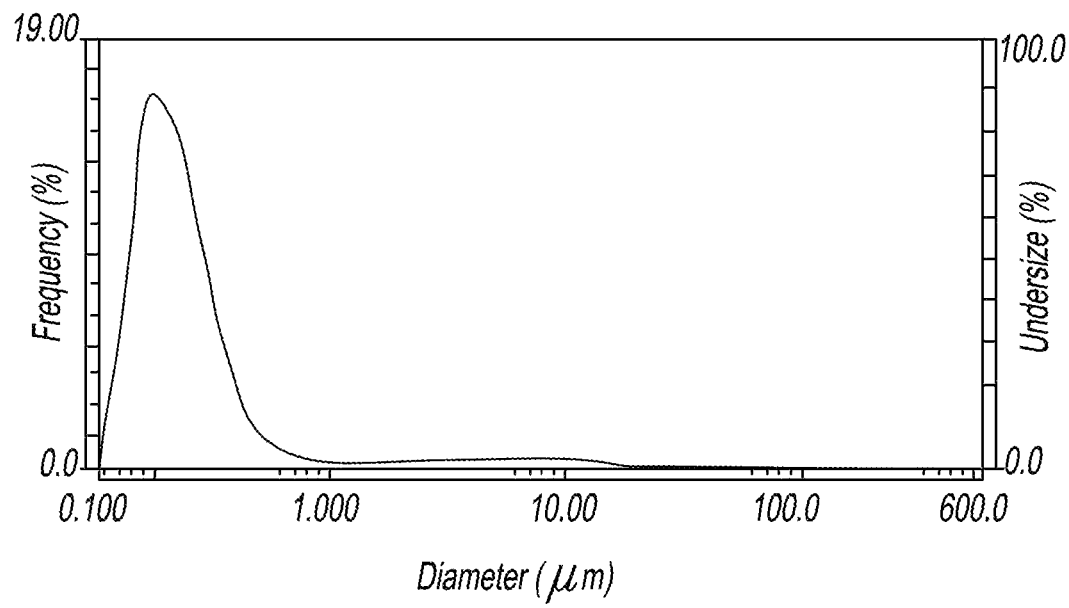
FIG. 2 with pH 7.4 and median particle size of 0.1844 μm with particles in each of FIG. 1 and FIG. 2 providing interstitial effectiveness for cell space application.

The foregoing descriptions of specific embodiments of the present invention have been presented for purposes of illustration and description. They are not intended to be exhaustive or to limit the present invention to the precise forms disclosed, and obviously many modifications and variations are possible in light of the above description and figures. The exemplary embodiment was chosen and described in order to best explain the principles of the present invention and its practical application for purposes of enabling others who are skilled in the art and making of the product to best utilize the present invention and various embodiments with various modifications as are suited to the particular use contemplated.

DETAILED DESCRIPTION OF THE INVENTION

A method of preparing a radioactive yttrium salt particle suspension comprising multiple steps comprising: using a hydrothermal process wherein a solution of soluble yttrium salt from the group of yttrium chloride, yttrium nitrate, yttrium sulfate, and yttrium bromide is combined with a solution of sodium phosphate having a stoichiometric excess of phosphate and pH when combined in the range of 1.5 to 8 and preferably pH in the range of 7 to 8.

Combining the solutions with continuous stirring and rapidly heating in a closed vessel to 150° C. and held for 1 to 10 hours to yield greater than 99.99% conversion of soluble yttrium to insoluble $YPO_4$ and to achieve the desired particle size distribution and;

Creating the desired particle size distribution of $YPO_4$ particles suspended in buffered saline at neutral pH suitable for direct injection into human or animal tissue.

The radioactive particle suspension wherein the particle size is less than 2 μm.

The radioactive particle suspension comprised of at least 90 percent of the total particle volume consisting of particles in the range of 0.1μ to 2 μm.

And further comprising: wherein the starting concentration of soluble yttrium in the combined solution is in the range of 0.5 to 3.0 mole/liter and the stoichiometric excess of phosphate ranges from 10 to 100%.

And further, comprising: the starting concentration of soluble yttrium in the combined solution is 0.08 moles/liter and the stoichiometric excess of phosphate is 25%.

The method further comprising: the particle suspension formed by preparing the particle precursor solution, mixing and heating to form the $YPO_4$ particles by controlled precipitation followed by post-processing the particles to achieve a suspension of $YPO_4$ particles in phosphate buffered saline solution at neutral pH suitable for injection into human or animal tissue.

The method further comprising: the particle suspension wherein the post processing consists of rinsing the particles 3 times with sterile phosphate buffered saline (PBS) solution and removing or adding PBS to achieve the final desired volume.

The method further comprising: the particle suspension wherein the post processing consists of adjusting the pH of the final solution with sodium hydroxide then removing excess solution or adding sterile PBS to achieve the final desired volume.

The method further comprising: the particle suspension wherein the yttrium phosphate particles are radioactive to serve as distributed sources of therapeutic radiation for treating cancerous tumors and other diseases and: making the particles radioactive by adding a small mass of soluble radioactive isotope to the particle precursor solution that becomes homogeneously incorporated into the insoluble yttrium phosphate particle matrix.

The method further comprising; the yttrium phosphate particle suspension wherein the particle concentration is in the range of 40 mg/ml to 125 mg/ml to facilitate imaging by x-ray computed tomography after being combined in a ratio of 1 to 4 by volume with biocompatible hydrogel or other suitable liquid carrier solution for injection into human or animal tissue.

Example I

One exemplary process for practicing the method of the present invention is shown below:

Step 1—preparing reagents by:

Step 1.1—weighing out a non-radioactive (i.e., Y-89) yttrium salt from the group of yttrium chloride, yttrium nitrate, yttrium sulfate, and yttrium bromide and transferring quantitatively to a volumetric flask; adding deionized water; agitating to mix completely; and Step 1.2—drawing up the $^{89}Y^{+3}$ solution from the volumetric flask into a syringe and pushing the solution through a filter and collecting the solution in a sterile container; and Step 1.3—preparing and filtering 0.15 M Na₂HPO4 and 0.05 M HCl reagents; storing the reagents at room temperature; and Step 2—preparing a radioactive $^{90}YCl_3$ solution by:

Adding to a source vial containing $^{90}YCl_3$ sufficient volume of 0.05 M HCl, to achieve recovery of the desired quantity of radioactive material from the source vial; and Step 3—performing a radioactive $(^{89}Y+^{90}Y)$ PO₄ synthesis procedure by:

Step 3.1—adding H₂O to the microwave reaction vial with a sterile magnetic stir bar; and placing the reaction vessel on a stir plate; and with continuous stirring;

Step 3.2—adding 0.15 M Na₂HPO₄; and

Step 3.3—adding $^{89}Y^{+3}$ solution; and

Step 3.4—adding $^{90}Y$ in 0.05 M HCl from a source vial; and

Step 3.5—recording the final pH; and

Step 3.6—transferring the vial to a microwave reactor; and

Step 3.7—setting the reaction temperature to a temperature in the range of 110° C. to 160° C. and reaction time to between one hour and 20 hours and starting the reactor;

Step 4—performing final steps comprising:

Step 4.1—placing the microwave vial with the particles in a centrifuge, subjecting the particles to centrifugation; and Step 4.2—removing the supernatant liquid and replacing it with sterile phosphate buffered saline, and repeating Steps 4.1 and 4.2 two additional times, and Step 4.3—removing excess supernatant liquid from the vial; and Step 4.4—properly labeling the vial.

Example II

Start with the method of Example I and add the following modifications and additions to the noted steps of Example I:

To Step 1.1—1.0 M $^{89}YCl_3$, weighing out non-radioactive (i.e., Y-89) YCl₃.6H₂O and transferring quantitatively to a volumetric flask; adding deionized water to the volumetric flash; agitating to mix completely; and Step 1.2—drawing up the 1.0 M $^{89}YCl_3$ solution into a syringe and pushing the solution through a filter and collecting the solution in a sterile container; and Step 3—radioactive $(^{90}Y+^{89}Y)$ PO₄ synthesis procedure;

Step 3.1—adding 1.0 ml of H₂O to the microwave reaction vial with a sterile magnetic stir bar and placing the reaction vessel on a stir plate and with continuous stirring;

Step 3.2—adding 2.67 ml of 0.15 M Na₂HPO₄; and

Step 3.3—adding 0.32 ml of $^{89}YCl_3$ solution; and

Step 3.4—adding up to 0.05 ml of $^{90}Y$ in 0.05 M HCl from a source vial; and

Step 3.5—recording the final pH and

Step 3.6—transferring the vial to a microwave reactor;

Step 3.7—setting the reaction temperature to 150° C. and reaction time to one hour and starting the reactor;

Step 4—final steps

Step 4.1—adjusting the pH of the product solution with 1.0 N NaOH to pH range of 1.5 to 8;

Step 4.3—removing supernatant leaving 1.0 ml in the vial for each scheduled tumor treatment.

Example III

Start with the method of Example II and add the following modifications and additions to the noted steps of Example II:

Step 1.1—1.0 M $^{89}YCl_3$: weighing out non-radioactive (i.e., Y-89) YCl₃6H₂O for a single scheduled tumor treatment to the nearest 0.01 g) 3.03±0.15 g and transferring quantitatively to a 10 ml volumetric flask; adding 10 ml deionized water to the 10 ml mark; agitating to mix completely; and Step 1.2—drawing up ~8-10 ml of 1.0 M $^{89}YCl_3$ into a syringe and pushing the solution through a filter and collecting the solution in a sterile container; and Step 1.3—preparing and filtering 0.15 M Na₂HPO₄ and 0.05 M HCl reagents; and Step 4—final steps Step 4.1—adjusting the pH of the product solution with 1.0 N NaOH to pH range of 7 to 8; and Step 4.2—removing supernatant leaving 1.0 ml in the vial for each scheduled tumor treatment.

Example IV

An alternate method of preparing a radioactive yttrium phosphate particle suspension comprises:

Using a hydrothermal process wherein a solution of yttrium salts from the group of yttrium chloride, yttrium nitrate, yttrium sulfate, and yttrium bromide is combined with a solution of sodium phosphate having a stoichiometric excess of phosphate and a pH when combined in the range of 1.5 to 8; combining the solutions with continuous stirring and heating in a closed vessel to the range of 110° C. to 160° C. and holding for 1 to 20 hours to yield greater than 99.99% conversion of soluble yttrium to insoluble YPO₄ and to achieve a particle size distribution wherein the particles are equal to or less than 2 um; and Creating the desired particle size distribution of YPO₄ particles suspended in buffered saline at neutral pH suitable for direct injection into human or animal tissue.

Example V

Start with the method of Example IV and add the following modifications and additions to the noted steps of Example IV:

The heating of the combined solutions is a rapid heating.

Example VI

Start with the method of Example V and add the following modifications and additions to the noted steps of Example V:

the radioactive particle suspension employed by the method comprises at least 90 percent of the total particle volume consisting of particles in the range of 0.1 μm to 2 μm.

Example VII

Start with the method of Example VI and add the following modifications and additions to the noted steps of Example VI:

employing a starting concentration of soluble yttrium in the combined solution that is in the range of 0.5 to 3.0 mole/liter and the stoichiometric excess of phosphate ranges from 10 to 100%.

Example VIII

Start with the method of Example VI and add the following modifications and additions to the noted steps of Example VI:

employing a starting concentration of soluble yttrium in the combined solution that is 0.08 moles/liter and the stoichiometric excess of phosphate is 25%.

Example IX

Start with the method of Example IV and add the following modifications and additions to the noted steps of Example IV:
mixing and heating the particle suspension formed by preparing the particle precursor solution to form the $YPO_4$ particles by controlled precipitation followed by post-processing the particles to achieve a suspension of $YPO_4$ particles in phosphate buffered saline solution at neutral pH suitable for injection into human or animal tissue.

Example X

Start with the method of Example IX and add the following modifications and additions to the noted steps of Example IX:
performing the post processing by rinsing the particles three times with sterile phosphate buffered saline (PBS) solution and removing or adding PBS to achieve the final desired volume.

Example XI

Start with the method of Example IX and add the following modifications and additions to the noted steps of Example IX:
Performing the post processing by adjusting the pH of the final solution with sodium hydroxide then removing excess solution or adding sterile PBS to achieve the final desired volume.

Example XII

Start with the method of Example IV and add the following modifications and additions to the noted steps of Example IV:
employing a particle suspension wherein the yttrium phosphate particles are radioactive to serve as distributed sources of therapeutic radiation for treating cancerous tumors and other diseases; and
making the particles radioactive by adding a small mass of soluble radioactive isotope to the particle precursor solution of Example IV that becomes homogeneously incorporated into the insoluble yttrium Example XIII Start with the method of Example IV and add the following modifications and additions to the noted steps of Example IV:
Using an yttrium phosphate particle suspension of Example IV wherein the particle concentration is in the range of 40 mg/ml to 125 mg/ml to facilitate imaging by x-ray computed tomography after being combined in a ratio of 1 to 4 by volume with biocompatible hydrogel or other suitable liquid carrier solution and injection into human or animal tissue; and
using a solution of sodium phosphate having a stoichiometric excess of phosphate and a pH in the range of 7 to 8.

What is claimed is:

1. A method of preparing a desired quantity of a radioactive yttrium phosphate particle suspension comprising:
using a hydrothermal process wherein a radioactive solution of yttrium salts from the group of yttrium chloride, yttrium nitrate, yttrium sulfate, and yttrium bromide is combined with a solution of sodium phosphate having a stoichiometric excess of phosphate and a pH when combined in the range 1.5 to 8, forming a combined solution by combining the solutions with continuous stirring and heating in a closed vessel to the range of 110° C. to 160° C. and held for 1 to 20 hours to yield greater than 99.99% conversion of soluble yttrium to insoluble $YPO_4$ and to achieve a particle size distribution wherein the particles are equal to or less than 2 μm; and
creating the desired particle size distribution of $YPO_4$ particles suspended in buffered saline at neutral pH suitable for direct injection into human or animal tissue;
preparing reagents by weighing out a non-radioactive (i.e., Y-89) yttrium salt from the group of yttrium chloride, yttrium nitrate, yttrium sulfate, and yttrium bromide and transferring quantitatively to a volumetric flask; adding deionized water, agitating to mix completely; and
drawing up an $^{89}Y^{3+}$ solution from the volumetric flask into a syringe and pushing the solution through a filter and collecting the solution in a sterile container; and
preparing and filtering 0.15 M $Na_2HPO_4$ and 0.05 M HCl reagents; storing the reagents at room temperature; and
preparing a radioactive $^{90}YCl_3$ solution by adding to a source vial containing $^{90}YCl_3$ a sufficient volume of 0.05 M HCl to achieve a recovery of a quantity of radioactive material from the source vial to achieve the desired quantity of the radioactive yttrium phosphate particle suspension; and
performing a radioactive ($^{90}Y+^{89}Y$) $PA_4$ synthesis procedure comprising:
adding $H_2O$ to a microwave reaction vial with a sterile magnetic stir bar and placing the reaction vessel on a stir plate; and with continuous stirring and adding 0.15 M $Na_2HPO_4$,
adding the $^{90}Y$ in solution from the source vial and the $^{90}Y^{3+}$ solution; and transferring the vial to a microwave reactor;
setting the reaction temperature to a temperature in the range of 110° C. to 160° C. and reaction time to between 1 hour and 20 hours and starting the reactor, and
taking final steps of placing the microwave vial with the particles in a centrifuge, subjecting the particles to centrifugation; and
removing the supernatant liquid and replacing the sterile phosphate buffered saline, and repeating the final steps two additional times; and
then removing excess supernatant liquid from the vial.

2. The method according to claim 1, wherein the $^{89}Y^{3+}$ solution is a 1.0 M $^{89}YCl_3$ solution;
the reaction is carried out at a temperature of 150° C. for one hour;
the pH of the product solution is adjusted to pH range of 1.5 to 8 with 1.0 N NaOH; and
the supernatant is removed to leave 1.0 ml in the vial for each scheduled tumor treatment.

3. The method according to claim 1 wherein a non-radioactive 1.0 M $^{89}YCl_3$ solution is prepared for single scheduled tumor treatment by adding to 3.03±0.15 g $^{89}$YCl$_3$6H$_2$O in a 10 ml volumetric flask and 10 ml deionized water to the 10 ml mark and agitating to mix completely; and the pH of the product solution is adjusted to a pH range of 7 to 8 with 1.0 N NaOH.

4. The method of claim 1 wherein the radioactive particle suspension created is comprised of at least 90 percent of the total particle volume comprising particles in the range of 0.1 μm to 2 μm; and wherein the starting concentration of soluble yttrium in the combined solution is in the range of 0.05 to 3.0 mole/liter and the stoichiometric excess of phosphate ranges from 10 to 100%.

5. The method of claim 4 wherein the starting concentration of soluble yttrium in the combined solution is 0.08 mole/liter and the stoichiometric excess of phosphate is 25%.

6. The method of claim 1 wherein the particle suspension is formed by mixing and heating said precursor solution to form the YPO$_4$ particles by controlled precipitation followed by post-processing the particles to achieve a suspension of YPO$_4$ particles in phosphate buffered saline solution at neutral pH suitable for injection into human or animal tissue; and wherein the post-processing of the particle suspension consists of rinsing the particles about 3 times with sterile phosphate buffered saline (PBS) solution and removing or adding PBS to achieve the final desired volume; and wherein the post-processing of the particle suspension consists of adjusting the pH of the final solution with sodium hydroxide then either removing excess solution or adding sterile PBS to achieve the final desired volume.

7. The method of claim 1 wherein the yttrium phosphate particles of the particle suspension are radioactive to serve as distributed sources of therapeutic radiation for treating cancerous tumors and other diseases; and making the particles radioactive by adding a small mass of soluble radioactive isotope to the particle precursor solution and homogeneously incorporating the isotopes there into to define an insoluble yttrium phosphate particle matrix.

8. The method of claim 1 wherein the particle concentration of the yttrium phosphate particle suspension is in the range of 40 mg/ml to 125 mg/ml to facilitate imaging by x-ray computed tomography after being combined in a ratio of about 1 to 4 by volume with biocompatible hydrogel or other suitable liquid carrier solution and injection into human or animal tissue and where the solution of sodium phosphate having a stoichiometric excess of phosphate and a pH in the range of 7 to 8.

9. A method of preparing a radioactive yttrium phosphate particle suspension having a desired particle size distribution of YPO$_4$ particles comprising:

using a hydrothermal process wherein a radioactive solution of yttrium salts from the group of yttrium chloride, yttrium nitrate, yttrium sulfate, and yttrium bromide is combined with a solution of sodium phosphate having a stoichiometric excess of phosphate and a pH when combined in the range 1.5 to 8, combining the solutions with continuous stirring and heating in a closed vessel to the range of 110° C. to 160° C. and held for 1 to 20 hours to yield greater than 99.99% conversion of soluble yttrium to insoluble YPO$_4$ and to achieve a particle size distribution wherein the particles are equal to or less than 2 μm, creating the desired particle size distribution of YPO$_4$ particles suspended in buffered saline at neutral pH suitable for direct injection into human or animal tissue;

preparing a radioactive $^{90}$YCl$_3$ solution by adding to a source vial containing $^{90}$YCl$_3$ a sufficient volume of 0.05 M HCl to achieve a recovery of a desired quantity of radioactive material; and performing a radioactive ($^{90}$Y+$^{89}$Y) PA$_4$ synthesis procedure further comprising:

adding H$_2$O to a microwave reaction vial with a sterile magnetic stir bar and placing the reaction vessel on a stir plate; and with continuous stirring and adding 0.15 M Na$_2$HPO$_4$, the $^{90}$Y in solution from the source vial and the $^{90}$Y$^{3+}$ solution to yield an admixture;

transferring the admixture to a reactor;

reacting the admixture at a temperature in the range of 110° C. to 160° C. and with a reaction time between 1 hour and 20 hours.

* * * * *